United States Patent
Lee et al.

(10) Patent No.: US 9,681,810 B2
(45) Date of Patent: Jun. 20, 2017

(54) FLUORESCENT IMAGE ACQUISITION AND PROJECTION APPARATUS AND METHOD FOR REAL-TIME VISUALIZATION OF INVISIBLE FLUORESCENT SIGNAL

(71) Applicant: Korea Photonics Technology Institute, Gwangju (KR)

(72) Inventors: Byeong-Il Lee, Gwangju (KR); In-Hee Shin, Gwangju (KR); Jae-Seok Park, Gyeongsangnam-do (KR); Joo-Beom Eom, Gwangju (KR); Hyung-Ju Park, Gwangju (KR); Seok-Ki Kim, Gyeonggi-do (KR)

(73) Assignee: Korea Photonics Technology Institute, Gwangju (KR)

( * ) Notice: Subject to any disclaimer, the term of this patent is extended or adjusted under 35 U.S.C. 154(b) by 587 days.

(21) Appl. No.: 13/968,964

(22) Filed: Aug. 16, 2013

(65) Prior Publication Data
US 2014/0052002 A1    Feb. 20, 2014

(30) Foreign Application Priority Data
Aug. 16, 2012  (KR) .................. 10-2012-0089481

(51) Int. Cl.
   *A61B 5/00*    (2006.01)
(52) U.S. Cl.
   CPC .......... *A61B 5/0071* (2013.01); *A61B 5/7271* (2013.01)
(58) Field of Classification Search
   CPC ..................... A61B 5/0071; A61B 5/7271
   See application file for complete search history.

(56) References Cited

U.S. PATENT DOCUMENTS

| | | | | |
|---|---|---|---|---|
| 2008/0287806 A1* | 11/2008 | Wood | ................... | A61B 5/0059 600/473 |
| 2009/0020709 A1* | 1/2009 | Yamaguchi | ............ | G01B 11/22 250/458.1 |
| 2011/0054327 A1* | 3/2011 | Kim | ..................... | A61B 5/0077 600/473 |

FOREIGN PATENT DOCUMENTS

| | | |
|---|---|---|
| JP | 2004-180834 A | 7/2004 |
| KR | 10-2007-0004821 | 1/2007 |
| KR | 10-2010-0066605 | 6/2010 |
| KR | 10-2011-0088676 A | 8/2011 |

OTHER PUBLICATIONS

International Search Report issued in corresponding application PCT/KR2013/007162, dated Sep. 23, 2013, pp. 1-4.

* cited by examiner

*Primary Examiner* — Ruth S Smith
(74) *Attorney, Agent, or Firm* — Brinks Gilson & Lione

(57) ABSTRACT

A fluorescent image acquisition and projection apparatus for real-time visualization of an invisible fluorescent signal is provided. The apparatus visualizes an invisible fluorescent signal generated from a target object (a tissue of a living body, a cell of a living body, or the like) by using a photodetection unit and a projector in real time. The apparatus directly projects a visualized fluorescent signal onto a region of the target object where the invisible fluorescent signal is generated, thereby enabling users to determine and confirm the generation location of the fluorescence with the naked eye.

5 Claims, 4 Drawing Sheets

FLUORESCENT IMAGE ACQUISITION AND PROJECTION APPARATUS AND METHOD FOR REAL-TIME VISUALIZATION OF INVISIBLE FLUORESCENT SIGNAL

PRIORITY

This application claims priority to Korean Application No. 10-2012-0089481, filed on Aug. 16, 2012, the disclosure of which is incorporated by reference herein by its entirety.

BACKGROUND

1. Technical Field

The present invention relates to a fluorescent image acquisition and projection apparatus. More specifically, the present invention relates to a fluorescent image acquisition and projection apparatus for real-time visualization of an invisible fluorescent signal, which can visualize an invisible fluorescent signal generated from a target object (a tissue of a living body, a cell of a living body, or the like) and directly project a visualized fluorescent signal back onto a region of the target object where the invisible fluorescent signal is generated, thereby determining a fluorescence generation location with the naked eye.

2. Related Art

Application fields of a fluorescence phenomenon have expanded from chemical measurement to phenomenal technical implementation. Imaging technology and measuring technology have been developed in the fields of medical research and molecular biological experiments using fluorescent signals and fluorescent images. Recently, various materials which can generate fluorescent signals with various wavelengths have been developed and applied to clinical and preclinical researches all over the world. Food and Drug Administration (FDA) approved some of those materials in clinical applications. With the development of various materials that generate fluorescence, technology for analyzing in vivo functions by using various light sources have been developed because fluorescent signals have a poor signal to noise ratio (SNR) and have the desirable penetration power with regard to a living body compared to light emission.

As molecular imaging has been actively researched, leading edge research using a fluorescence phenomenon has been carried out. Fluorescence can be readily implemented as a system for utilizing fluorescence can be implemented with simpler devices, such as an excitation light source, a band-pass filter, and a photodetector, than other detection devices. Thus, fluorescence technology may be cost-effective. In particular, when a fluorescence material having an emission signal in the visible light region from 400 to 700 nm is used, observation with the naked eye is available, and the penetration power with respect to the skin is desirable. Thus, a medical use of such fluorescence materials is increasing.

Fluorescence signals have poor SNR and relatively limited sensitivity. Emitted fluorescence signals have relatively high intensity, but fluorescence intensity decreases due to optical phenomena such as the scattering, absorption and so on which may occur when fluorescence signals in the visible light region are generated inside a living body. In order to resolve these problems, research on the development of near-infrared fluorescence materials having emitted signals in the rear-infrared region is being actively carried out because near-infrared light in the 780 to 2000 nm region has desirable penetration power characteristics compared to the visible light in the living body. Furthermore, due to the advantage of acquiring a signal related to depth information, an examination method applied to preclinical and clinical trials is under development.

As a method used in preclinical trials, a material that is mixed with a fluorescence material and a target probe which can be targeted at a disease is developed and is injected through intravenous injection. Then morphological characteristics of a tumor can be observed and the progress of the treatment is carried out. Also, this method can be widely used to evaluate clinical characteristics related to soft tissues. As a representative agent, indocyanine green (ICG), a near-infrared fluorescence agent approved by the FDA, is used as a vascular contrast medium for determining the extent of circulation in blood vessels. ICG is recently used to determine locations of sentinel lymph nodes (SNs) indicative of the extent of metastasis of tumors in the case of a breast cancer patient prior to the lumpectomy.

However, in the case of the implementation of near-infrared fluorescence, a near-infrared band-pass filter and a photodetection device are additionally required. In addition, images devices may be needed to determine image information such as shape, location and strength of fluorescence. Due to these limitations related to the implementation of near-infrared fluorescent images, technical improvements in near-infrared fluorescence imaging may be needed.

BRIEF SUMMARY

In order to overcome the above related art, the main objective of the present invention is to implement fluorescence using near-infrared light as emitted signals, to convert an invisible near-infrared fluorescence signal to a visible signal and to project an image of a subject in the form of a visible image signal. Another objective of the present invention is to employ a small-sized photodetection element and a projector, thereby integrating the photodetection element and the projector with a near-infrared band light source into a single unit. This single unit can be used as near-infrared band image implementation equipment. Still another objective of the present invention is to provide a method of directly observing a fluorescent image with the naked eye, thereby overcoming drawbacks of conventional indirect observation of a fluorescent image through a monitor in a clinical trial, preclinical trial or surgery using a fluorescent image and providing a convenient, easy and direct method of observing a fluorescent image. The objectives of the present invention are not limited to the above-described objectives, and other objectives that have not been described will be apparent to those who are skilled in the field based on the following description.

One embodiment of a fluorescent image acquisition and projection apparatus includes a plurality of light sources configured to generate invisible fluorescence, a detection unit located at a center of the light sources and operable to acquire an invisible fluorescent image from a target, and a projector unit located at the center of the light sources and operable to project a visible fluorescent image onto the target.

One embodiment of a fluorescent image acquisition and projection method includes (i) an invisible light generation step of generating, by light sources, invisible fluorescence under control of a control device, (ii) an invisible fluorescent image signal acquisition step of obtaining, by a detection unit, a signal of the invisible fluorescent image from a target object following the invisible light generation step, (iii) an image signal processing step of receiving from the detection unit and processing, by the control device, the invisible fluorescent image signal of the target object into a visible fluorescent signal, and transmitting, by the control device, the visible fluorescent signal to a projector unit and (iv) a visible fluorescent signal projection step of projecting, by the projector unit, the visible fluorescent signal onto the target object.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE DRAWINGS AND THE PRESENTLY PREFERRED EMBODIMENTS

Figure 1:
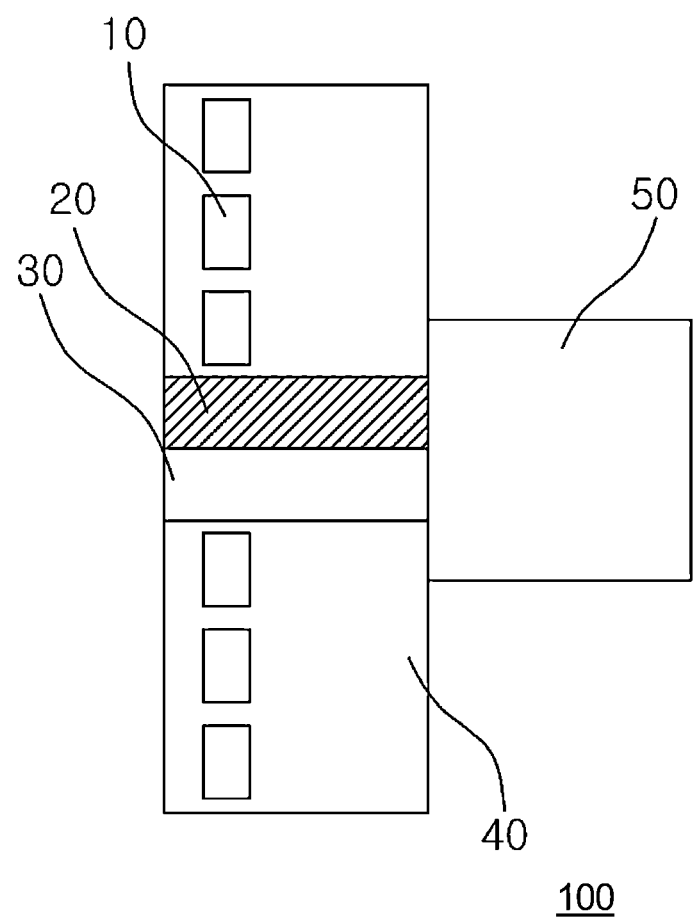
FIG. 1 is a diagram showing one embodiment of a fluorescent image acquisition and projection apparatus using a photodetection element and a projector according to the present invention.

ICG is a fluorescent agent that can be clinically applied as it was approved by the FDA. ICG has the optical characteristics of absorbing near-infrared light in the 750 nm band and generating near-infrared fluorescence in the 820 nm band. Due to these optical characteristics of ICG, a band-pass filter and a photodetection element which are used in near-infrared region, can be used to detect fluorescence signals. Furthermore, application to clinical and preclinical trials is desired due to the proven characteristics of ICG. A fluorescent image cannot be observed with the naked eye because of the near-infrared characteristics of ICG. Fluorescence signals can be checked and confirmed by using a near-infrared band-pass filter and a photodetection element when applied to clinical and preclinical trials. Embodiments described below may overcome the drawback of the conventional near-infrared fluorescence imaging and provide improved convenience and ease in use.

In one embodiment, a fluorescent image in a near-infrared band acquired by the photodetection element is transferred to a projector, the fluorescent image is projected, and thus the fluorescent image is visualized at the generation location of fluorescence. Accordingly, the generation of the fluorescence can be checked with the naked eye.

In another embodiment of the present invention, a fluorescent image acquisition and projection apparatus is provided. The apparatus includes light sources configured to generate invisible fluorescence; a detection unit located at the center of the light sources and configured to acquire an invisible fluorescent image from a target; and a projector unit located at the center of the light sources and configured to project a visible fluorescent image onto the target. In further another embodiment, the fluorescent image acquisition and projection apparatus may further include an apparatus casing configured such that the light sources are located on the front thereof and the detection unit and the projector unit are located at the center of the light sources.

In further another embodiment, the fluorescent image acquisition and projection apparatus may further include a band-pass filter located in front of the detection unit, a signal of the fluorescent image implemented from the target object may be filtered by the band-pass filter, and the filtered fluorescent image may be acquired by the detection unit. In further another embodiment, the detection unit may be formed of any one of an array-type photodiode, a digital camera element, a diode-type photodetection element, and a photoconductor-type photodetection element. The projector unit may project a fluorescent image signal onto the target object, and may perform zooming, focus adjustment, and projection location adjustment.

In further another embodiment, the fluorescent image acquisition and projection apparatus may further include a control device configured to cause the light sources to generate invisible light, to receive the signal detected by the detection unit, and to transmit a fluorescent image signal to the projector unit. The control device may include an image conversion processing unit configured to process the signal of the acquired image of the target object that is transmitted from the detection unit based on the generation of fluorescence of the light sources under a control of the control device; a projection image processing unit configured to convert the image obtained by the image conversion processing unit into a projection image in order to transmit the image to the projector unit; and a monitor image output unit configured to process the image signal of the target object in order to transmit the image signal to a monitor.

One embodiment of a fluorescent image acquisition and projection method includes (i) an invisible light generation step of generating, by light sources, invisible fluorescence under the control of a control device; (ii) an invisible fluorescent image signal acquisition step of obtaining, by a detection unit, the signal of the invisible fluorescent image from a target object following the invisible light generation step; (iii) an image signal processing step of processing, by the control device that receives the invisible fluorescent image signal of the target object from the detection unit, the image signal, and transmitting, by the control device, a visible fluorescent signal to a projector unit; and (iv) a visible fluorescent signal projection step of projecting, by projector unit, the visible fluorescent signal onto the target object.

The image signal processing step may include (i) a color information determination step of determining the color information of the target object; (ii) a corresponding color information extraction step of extracting color information corresponding to the color information of the target object from a color information table of memory; (iii) an image information conversion step of converting the image information acquired from the target object into the color information corresponding to the target object obtained at the corresponding color information extraction step; and (iv) a converted image information transmission step of transmitting the converted image information, obtained by converting the image information into the color information corresponding to the target object, to a projector.

In the described embodiments, an excitation light source for the generation of near-infrared fluorescence, a photodetection element for the acquisition of a fluorescent image, and a projector for the projection of a fluorescent image are integrated into a single system, and thus there are considerable advantages of achieving the composite functionality in a single system.

Another advantage of the present invention is (i) to acquire a near-infrared fluorescent image, generated by the absorption of light and the emission of long-wavelength transitioned fluorescence from a target object into which a near-infrared fluorescent agent has been injected, by using a photodetection element, and (ii) to project the acquired fluorescent image back onto the same location of the target object by using the projector, by using the imaging apparatus configured as described above. Accordingly, the naked eye confirmation of the generation of near-infrared fluorescence becomes available.

Still another advantage of the present invention is to visualize the location and shape of the generation of fluorescence to be accurately determined and confirm in a clinical trial or surgery using near-infrared fluorescence, thereby allowing the above described embodiments of apparatus and the method to be effectively utilized in clinical trials and surgery.

An example of the illustrative configuration and operation of an invisible fluorescent image acquisition and projection apparatus for real-time visualization of fluorescent signals according to the present invention will be described with reference to the accompanying drawings below.

Although general terms currently widely used are selected as the terms used herein as much as possible, some terms are randomly selected by the applicant in specific cases, in which case the meanings thereof should be determined based on the meanings that are described and used in the detailed description of the present invention, rather than simply based on the names of the terms. Furthermore, the present invention is not limited to the described embodiments, and may be embodied in other forms. Throughout the specification, the same reference numerals may be viewed as designating the same elements.

FIGS. 1-4 illustrate one embodiment of an invisible fluorescent image acquisition and projection apparatus 100 for real-time visualization of fluorescent signals. The apparatus 100 includes a light source 10 operable to generate invisible fluorescence, a detection unit 20 operable to acquire a fluorescent image, and a projector unit 30 operable to project a fluorescent image. The fluorescent image acquisition and projection apparatus 100 is provided to acquire an image signal of a subject in the form of a fluorescent signal, analyze and process the acquired image signal, and project the image signal, thereby implementing an image back onto the subject. The detection unit 20 is located adjacent to the light source 10, and the projector unit 30 located adjacent to the detection unit 20 as shown in FIG. 1.

When a target or a target object, from which a signal of a fluorescent image is acquired, is located inside a skin or a living body of a subject, an image signal is projected back onto the subject to enable an image to be observed from the outside of the skin or living body of the subject, and thus a user can easily determine the shape of the subject located inside the skin or living body by observing the image projected onto the outside surface of the skin or living body of the subject. In this embodiment, the target may include objects such as one or more tissues, or one or more cells present inside of a skin or a living body of the subject. For instance, the target may be cancerous tissues or cells that generate a fluorescent signal and the subject may be a small animal or a human body which contains cancerous tissues or cells.

As described above, a signal of a target which is actually difficult to observe is obtained through the acquisition of a fluorescent image, is subjected to signal processing, and is projected back onto the subject. Thus, the location or shape of the subject can be easily determined. Therefore, a following treatment process can be easily performed.

Furthermore, when an image signal is acquired, a visible fluorescent signal or an invisible fluorescent signal may be used. In particular, it is preferable to acquire an image signal using an invisible fluorescent signal. This is because the image signal of a subject is initially acquired through an invisible fluorescent signal and then a visible projector image signal is projected onto the subject. Accordingly, users can easily determine the shape of the subject without confusion between two image signals, i.e., an invisible fluorescent signal and a visible projector image signal, compared to the case where users observe two image signals with the naked eye. Therefore, preferably, invisible light is applied to generate fluorescence from the light source 10 and the detection unit 20 acquires a fluorescent image, while a projector image signal is obtained by processing the acquired image signal and projected back onto the subject as a visible image signal.

Figure 2:
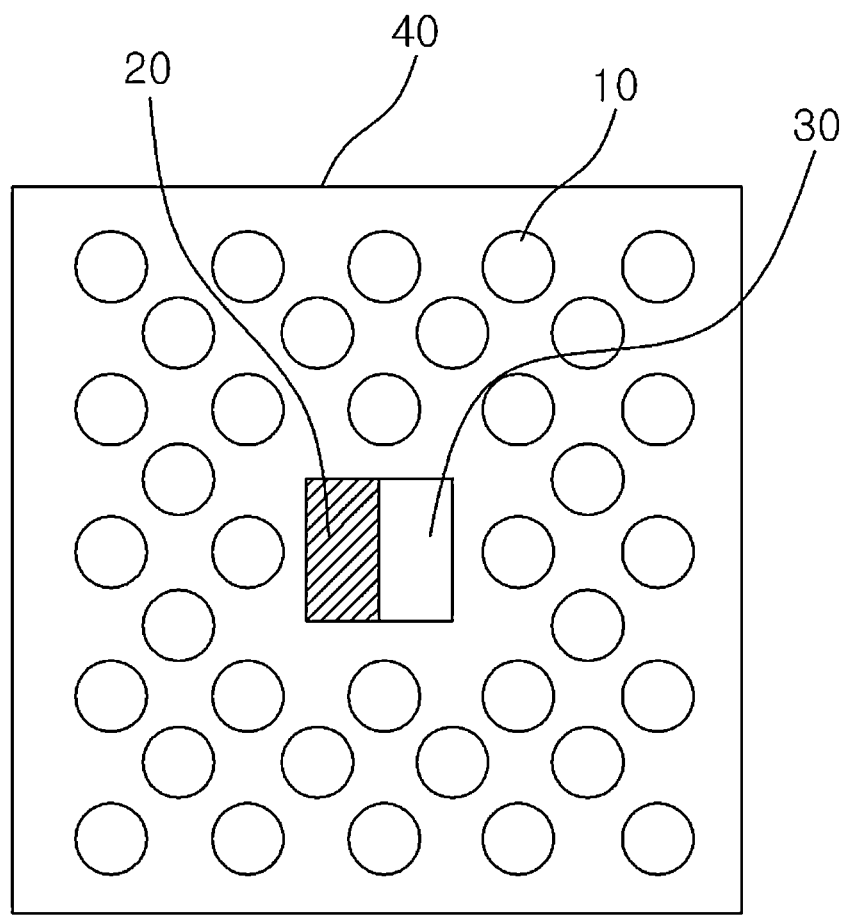
FIG. 2 is a diagram showing the fluorescent image acquisition and projection apparatus of FIG. 1 which is viewed from the direction of a subject.

As shown in FIGS. 1 and 2, it is preferred that the fluorescent image acquisition and projection apparatus 100 includes a plurality of light sources 10 that generates invisible fluorescence. In this embodiment, as shown in FIG. 2, the detection unit 20 is located at the center of the plurality of light sources 10 and acquires an invisible fluorescent image from a target. In this embodiment, the projector unit 30 is located at the center of the plurality of light sources 10 and projects a visible fluorescent image onto the target.

The light sources 10 generate an invisible fluorescent signal and the detection unit 20 acquires a fluorescent image which is preferably a near-infrared fluorescent signal that is between 750 nm and approximately 3,000 nm. The fluorescent image projected onto a target object via the projector unit 30 may pertain to a visible range.

In this embodiment, as shown in FIGS. 1 and 2, the plurality of light sources 10 are located on the front of an apparatus casing 40 and the detection unit 20 and the projector unit 30 are located at the center of the plurality of light sources 10. In other embodiment, different arrangements and configuration are available. Accordingly, one or the plurality of light sources 10 are installed on the apparatus casing 40 in the direction of the target object and emit an invisible fluorescent signal to the target object. The detection unit 20 detects a signal of a fluorescent image from the target object through the operation of the light source 10. The detection unit 20 is installed inside the apparatus casing 40. The signal of the fluorescent image acquired by the detection unit 20 is transmitted to a control device 50, and a visible image signal projected back onto the target object is transferred to the projector unit 30 and projected onto the target object. This projector unit 30 is installed inside the apparatus casing 40.

Accordingly, the light sources 10, the detection unit 20, and the projector unit 30 are all located in the single apparatus casing 40, and thus the acquisition and projection of a fluorescent image signal, such as the acquisition of an image signal from the target object and the projection of a shape-related image signal onto the target object, can be performed.

In addition, a band-pass filter is located in front of the detection unit 20. The signal of the fluorescent image generated from the target object is filtered by the band-pass filter, and the filtered fluorescent image is acquired by the detection unit 20. Accordingly, unnecessary noise is removed, and a clear image signal of the subject can be obtained. In one embodiment, the detection unit 20 may be formed of array-type photodiodes, or a digital camera element. In another embodiment, the detection unit 20 may be formed of any one of a diode-type photodetection element and a photoconductor-type photodetection element.

Furthermore, the projector unit 30 projects the signal of the fluorescent image onto the target object, and may be provided to perform zooming, auto focusing, projection location adjustment, etc. For this purpose, a zoom function unit, a focus adjustment unit, and a location adjustment unit may be provided together.

In this embodiment, the fluorescent image acquisition and projection apparatus 100 includes a control device 50 which is operable to cause the light source 10 to generate invisible light, to receive the signal detected by the detection unit 20, and to transmit the signal of the fluorescent image to the projector unit 30. The control device 50 includes a processor and a memory. In one embodiment, the control device 50 is integrated with the apparatus 100 as shown in FIG. 1. In another embodiment, the control device 50 may be arranged to be separate from the apparatus 100. Various arrangements and configuration of the control device 50 are available as long as the control device 50 operates to control the transmission and reception of a detected signal, signal analysis, and the transmission and reception of the projector signal through wired or wireless signal transmission.

Figure 4:
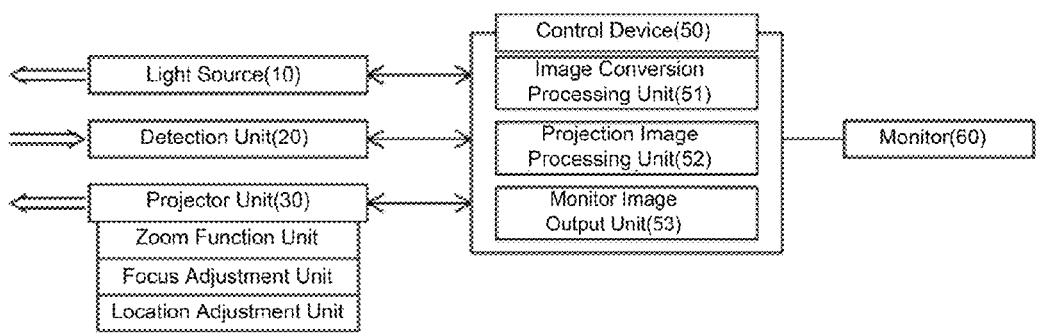
FIG. 4 is a control configuration diagram illustrating operations of the fluorescent image acquisition and projection apparatus of FIG. 1.

In this embodiment, the control device 50 includes an image conversion processing unit 51, as shown in FIG. 4. The image conversion processing unit 51 processes the signal of the acquired image of the target object that is transmitted from the detection unit 20 based on the generation of fluorescence of the light sources 10 under the control of the control device 50. In particular, in generating the fluorescent signal through the light sources 10, elements that emit invisible light are included together, and these invisible light emitting elements emit light. Also in the detection unit 20, the photodetection elements may be formed of elements that are capable of detecting optical signals in the invisible light region.

As shown in FIG. 4, the control device 50 also includes a projection image processing unit 52 that converts the image obtained by the image conversion processing unit 51 into a projection image in order to transmit the projection image to the projector unit 30. Accordingly, an optical signal in the invisible light region is detected by the detection unit 20, the signal of the image is analyzed, and accordingly, the image signal of the target object is extracted. Thereafter, the image signal is transmitted to the projector unit 30, and is then projected onto the target object in the form of an optical signal in the visible light region.

Additionally, the control device 50 may include a monitor image output unit 53 that processes the image signal of the target object in order to transmit the image signal to a monitor 60, as shown in FIG. 4. Therefore, users may check the image of the target object displayed on the monitor 60. A configuration related to ON/OFF manipulation of users may be included with the projector unit 30. In another embodiment, the image signal for the projection may be implemented to be projected with a conspicuous color different from a skin color of the target object.

Figure 3:
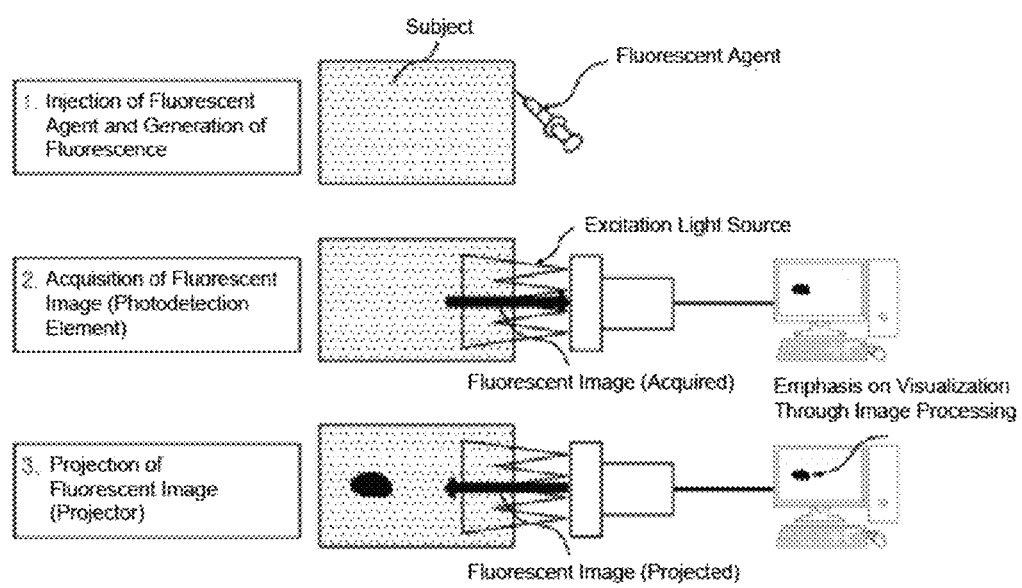
FIG. 3 is a diagram illustrating an operating principle of the fluorescent image acquisition and projection apparatus as shown in FIGS. 1 and 2.
Figure 5:
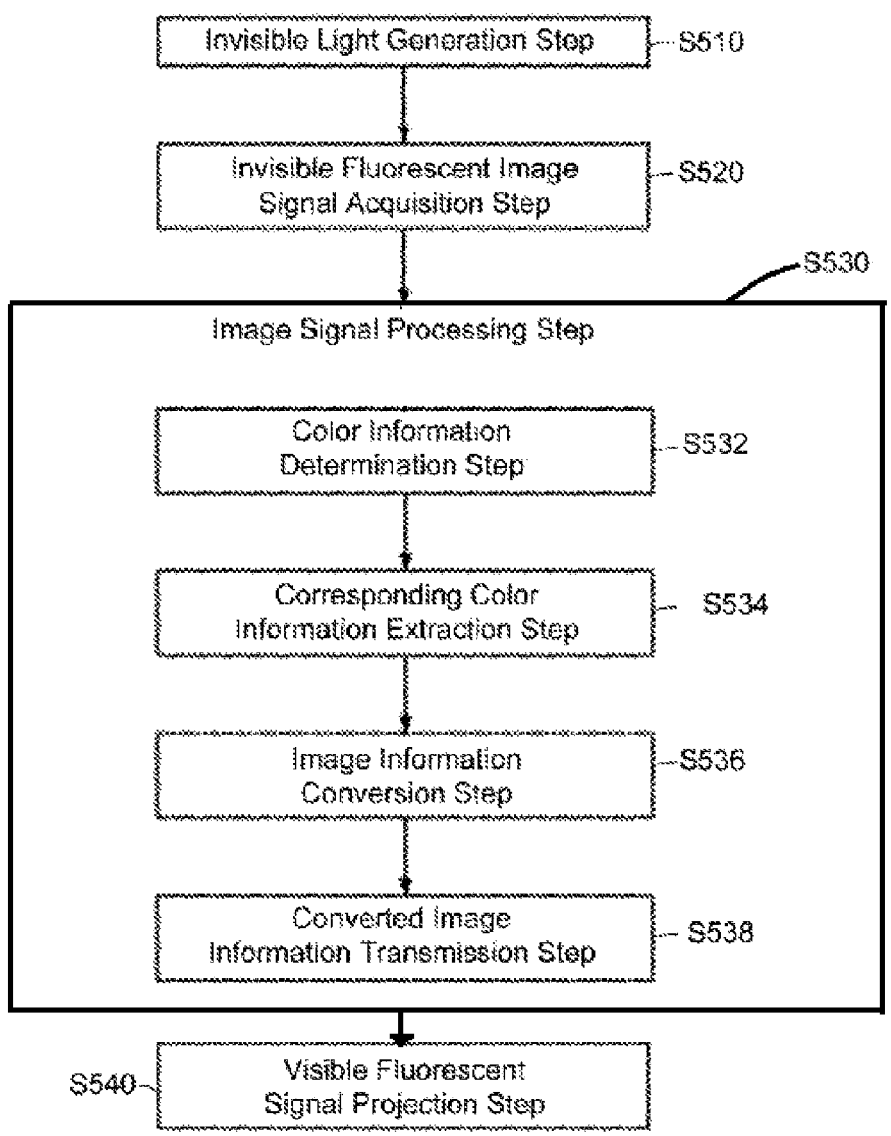
FIG. 5 is a flowchart illustrating one embodiment of a method for acquiring and projecting a fluorescent image.

Referring to FIG. 5, one embodiment of a fluorescent image acquisition and projection method based on the above-described apparatus 100 will be described below. As illustrated in FIG. 3, a fluorescent agent is injected into a subject, and thus a fluorescent image can be acquired through the generation of fluorescence.

FIG. 5 illustrates an invisible light generation step (S510) at which the light sources 10 generate invisible fluorescence under the control of the control device 50. It will be apparent that users cannot observe the subject and the light of fluorescence with the naked eye because the fluorescence of invisible light is emitted. Preferably, the invisible light used in this embodiment is a near-infrared fluorescent signal which is above 750 nm band.

Following the invisible light generation step (S510) based on the generation of the fluorescence, an invisible fluorescent image signal acquisition step (S520) at which the detection unit 20 obtains the signal of the invisible fluorescent image from the target object is performed as shown in FIG. 5.

In connection with this, an image signal processing step (S530) at which the control device 50 that receives the invisible fluorescent image signal of the target object from the detection unit 20 processes the image signal and transmits a visible fluorescent signal to the projector unit 30 is performed. Thereafter, a visible fluorescent signal projection step (S540) at which the projector unit 30 projects the visible fluorescent signal onto target object is performed. Accordingly, users can observe and confirm the shape and location of the subject with the naked eye while observing a visible fluorescent image projected onto the target object.

Referring to FIG. 5, the image signal processing step (S530) is described in detail. A color information determination step (S532) that determines color information of the target object is performed. Based on this, a corresponding color information extraction step (S534) that extracts color information from the color information table of a memory is performed. The image signal processing step (S530) and the color information determination step (S532) are performed to implement an image using the color information corresponding to the target object so that the subject image projected onto the target object can be more easily observed with the naked eye.

Accordingly, an image information conversion step (S536) that converts the image information acquired from the target object into the color information corresponding to the target object obtained at the corresponding color information extraction step is performed. Thereafter, a converted image information transmission step (S538) transmits the converted image information obtained by converting the image information into the color information corresponding to the target object to the projector (S536). The projector unit 30 receives the converted image information and projects the signal of the visible fluorescent image onto the target object, and thus users perform a treatment while observing the image of the subject projected onto the surface of the target object, that is, the skin or living body.

In the above described embodiments, the fluorescent image acquisition and projection apparatus 100 using a photodetection element and a projector, includes the light sources 10, the photodetection unit 20, the projector unit 30, the apparatus casing 40, and the control device 50 operable to control the light sources, the photodetection element and the projector, as illustrated in FIG. 1. The apparatus is configured to integrate the light sources 10, the photodetection unit 20 and the projector unit 30 into a single system, as illustrated in FIG. 2.

Furthermore, a band-pass filter corresponding to the wavelength of the generated fluorescent image is located in front of the photodetection element of the detection unit 20, as illustrated in FIG. 2, and the projector 30 includes an automatic focus function and a zoom function in order to adjust the size and focus of an image. Furthermore, the operation of the light sources, the acquisition of the image of the photodetection element and the operation of the projector can be implemented by using the light sources, the photodetection element, the projector and the control device 50, as illustrated in FIG. 1.

The operating principle of the fluorescent image acquisition and projection apparatus, that is, the apparatus for implementing and projecting a fluorescent image by using a photodetection element and a projector, may be illustrated as in FIG. 3, which may be summarized as follows. The light generated by the light sources 10 is absorbed into a target object into which a fluorescent agent has been injected, and the absorbed light is emitted from the target object in the form of long-wavelength shifted fluorescence. The fluorescence emitted as described above is detected by the photodetection element (detection unit 20), and then a fluorescent image acquired by the photodetection element is converted into an image in which that a visualization function can be emphasized via data processing. The converted image is transferred to the projector unit 30 and projected back into a location identical to a location where the fluorescence of the target object was generated.

Furthermore, the photodetection element consists of a band-pass filter suitable for the wavelength of the fluorescence emitted from the target object, and the projector has an automatic focus function and a zoom function so that the size and focus of a fluorescent image projected into a target object are consistent with those of a fluorescent image that is generated in the target object.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A fluorescent image acquisition and projection apparatus, comprising:
   a plurality of light sources that generate light;
   a detection unit comprising a photodetection element and located at a center of the light sources and operable to acquire an invisible fluorescent image from a target object where a fluorescent agent has been injected into a region of the target object,
   wherein the light generated by the light sources is absorbed into the target object and the absorbed light is emitted from the region of the target object in the form of long-wavelength shifted fluorescence;
   wherein the detection unit detects the long-wavelength shifted fluorescence emitted from the region of the target object and acquires the invisible fluorescence image;
   a projector unit located at the center of the light sources and that is configured to project a visible fluorescent image directly onto the region of the target object where the long-wavelength shifted fluorescence of the target object has been generated such that the shape and the location of the region of the target object are observed and confirmed with the naked eye while observing the visible fluorescent image projected onto the region of the target object;
   a control device comprising a processor and a memory and operable to:
      control the light sources to generate the light;
      receive a fluorescent image signal indicative of the invisible fluorescent image acquired by the detection unit,
      process in real-time the fluorescent image signal by converting the fluorescent image signal to a projection image signal indicative of the visible fluorescent image, wherein processing the fluorescent image signal further comprises analyzing the fluorescent image signal and extracting a shape-related image signal;
      transmit the projection image signal to the projector unit; and
      process the fluorescent image signal of the target object and transmit the processed signal to a monitor such that the monitor displays the target object; and
   an apparatus casing housing the light sources, the detection unit and the projector unit such that the light sources are located on a front thereof and the detection unit and the projector unit are located at the center of the light sources.

2. The fluorescent image acquisition and projection apparatus of claim 1, further comprising:
   a band-pass filter located in front of the detection unit and operable to filter the invisible fluorescent image from the target object, and
   wherein the detection unit acquires a filtered fluorescent image.

3. The fluorescent image acquisition and projection apparatus of claim 1, wherein the projector unit is configured to:
   perform zooming, focus adjustment, and projection location adjustment.

4. A fluorescent image acquisition and projection method, comprising:
   injecting a fluorescent agent into a region of a target object;
   generating, with a plurality of light sources, invisible fluorescence under control of a control device, wherein the control device comprises a processor and a memory;
   obtaining, with a detection unit comprising a photodetection element and located at a center of the light sources, an invisible fluorescent image from the target object;
   wherein the light generated by the light sources is absorbed into the target object and the absorbed light is emitted from the region of the target object in the form of long-wavelength shifted fluorescence;
   wherein obtaining the invisible fluorescent image comprises detecting long-wavelength shifted fluorescence emitted from the region of the target object and acquiring the invisible fluorescence image;
   receiving a fluorescent image signal indicative of the invisible fluorescent image acquired by the detection unit;
   processing with the control device in real-time the fluorescent image signal by converting the fluorescent image signal to a projection image signal indicative of a visible fluorescent image, wherein processing in real time the fluorescent image signal comprises analyzing the fluorescent image signal and extracting a shape-related image signal;

transmitting, by the control device, the projection image signal to a projector unit, wherein the projector unit is located at the center of the light sources;

projecting, by the projector unit, the visible fluorescent image directly onto the region of the target object where the long-wavelength shifted fluorescence of the target object has been generated, such that the shape and the location of the region of the target object are observed and confirmed with the naked eye while observing the visible fluorescent image projected onto the region of the target object; and processing the fluorescent image signal of the target object for displaying on a monitor and transmitting the processed signal to the monitor.

5. The fluorescent image acquisition and projection method of claim 4, wherein processing in real time the fluorescence image signal further comprises:

determining color information of the target object;

extracting color information corresponding to the color information of the target object from a color information table stored in a memory;

converting image information acquired from the target object into the color information corresponding to the target object; and transmitting the converted image information to the projector unit.

* * * * *